(12) United States Patent
Persson

(10) Patent No.: US 6,248,056 B1
(45) Date of Patent: Jun. 19, 2001

(54) METHOD AND AN APPARATUS FOR TREATING TUMORAL DISEASES (CANCER)

(76) Inventor: Bertil Persson, Angantyrsgränd 19, SE-224 75 Lund (SE)

( * ) Notice: Subject to any disclaimer, the term of this patent is extended or adjusted under 35 U.S.C. 154(b) by 0 days.

(21) Appl. No.: 09/269,119

(22) PCT Filed: Oct. 1, 1997

(86) PCT No.: PCT/SE97/01656

§ 371 Date: Mar. 19, 1999

§ 102(e) Date: Mar. 19, 1999

(87) PCT Pub. No.: WO98/14238

PCT Pub. Date: Apr. 9, 1998

(30) Foreign Application Priority Data

Oct. 1, 1996 (SE) .................................................. 9602799

(51) Int. Cl.[7] .................................................. A61N 5/00
(52) U.S. Cl. .................................................. 600/1
(58) Field of Search .................................. 600/1, 2, 3, 4, 600/5, 6, 7, 8, 9, 10, 11, 12, 13, 14, 15; 250/492.3

(56) References Cited

U.S. PATENT DOCUMENTS

| | | | |
|---|---|---|---|
| 4,100,920 | * 7/1978 | Le Goaster | 128/172.1 |
| 4,226,246 | * 10/1980 | Fragnet | 128/420 |
| 4,690,130 | 9/1987 | Mirell | 600/2 |
| 4,705,955 | 11/1987 | Mileikowsky | 600/1 |
| 4,989,605 | * 2/1991 | Rossen | 128/422 |
| 5,183,456 | 2/1993 | Liboff et al. | 600/9 |
| 5,211,622 | 5/1993 | Liboff et al. | 600/9 |
| 5,304,207 | * 4/1994 | Stromer | 607/3 |
| 5,349,198 | 9/1994 | Takanaka | 250/492.3 |
| 5,437,600 | 8/1995 | Liboff et al. | 600/9 |
| 5,585,643 | 12/1996 | Johnson | 600/1 |
| 5,871,708 | 2/1999 | Park et al. | 600/1 |

FOREIGN PATENT DOCUMENTS

| | | | |
|---|---|---|---|
| 666191 | * 7/1988 | (CH) | . |
| 4007562 | * 9/1991 | (DE) | . |
| 0236285 | 9/1987 | (EP) | . |
| 0407057 | * 1/1991 | (EP) | . |
| 0646392 | * 3/1995 | (EP) | . |
| 2160427 | 12/1985 | (GB) | . |
| 9405370 | * 3/1994 | (WO) | . |

OTHER PUBLICATIONS

Translation of Abstract DE 40 07 562.*
Translation of Abstract CH 666 199.*

* cited by examiner

Primary Examiner—Eric F. Winakur
Assistant Examiner—Brian Szmal
(74) Attorney, Agent, or Firm—Ladas and Parry

(57) ABSTRACT

An apparatus (40) according to the invention includes a radiation emitter (34) for ionizing radiation and a high voltage generator (1) for generating brief voltage pulses for voltage application of electrodes (6, 15, 16, 24) included in the apparatus. The electrodes are designed to be secured at or introduced into tissue in a restricted region of a human or an animal and to form between them an electric field in the tissue. The radiation emitter (34) is provided to emit ionizing radiation to a tumor in the tissue in that region which is to be treated, while the electrodes (6, 15, 16, 24) are disposed to be placed in or at the tumor in order that the electric field pass through the tumor.

16 Claims, 15 Drawing Sheets

RAT WITH AN UNTREATED TUMOR

RAT WITH TUMOR 47 DAYS AFTER SOLELY RADIATION TREATMENT OF THE TUMOR WITH 4 x 2Gy$^{60}$Co GAMMA RADIATION

RAT WITH TUMOR 47 DAYS AFTER ELECTRODYNAMIC RADIATION TREATMENT OF THE TUMOR: 4 x (2Gy, PLUS 16 ELECTRICAL PULSES (1300 V/cm, 1 ms, 1s$^{-1}$))

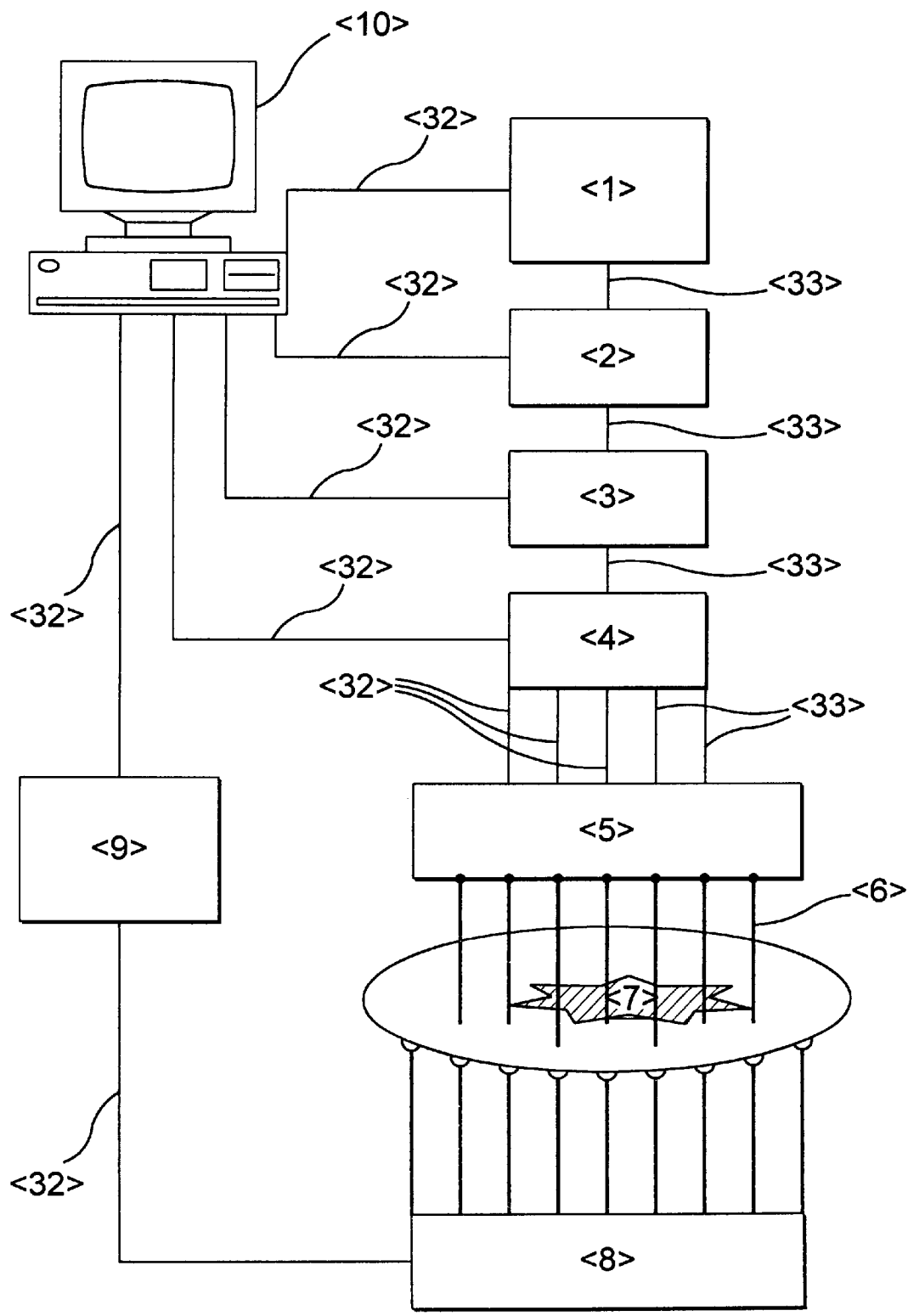
F I G. 5

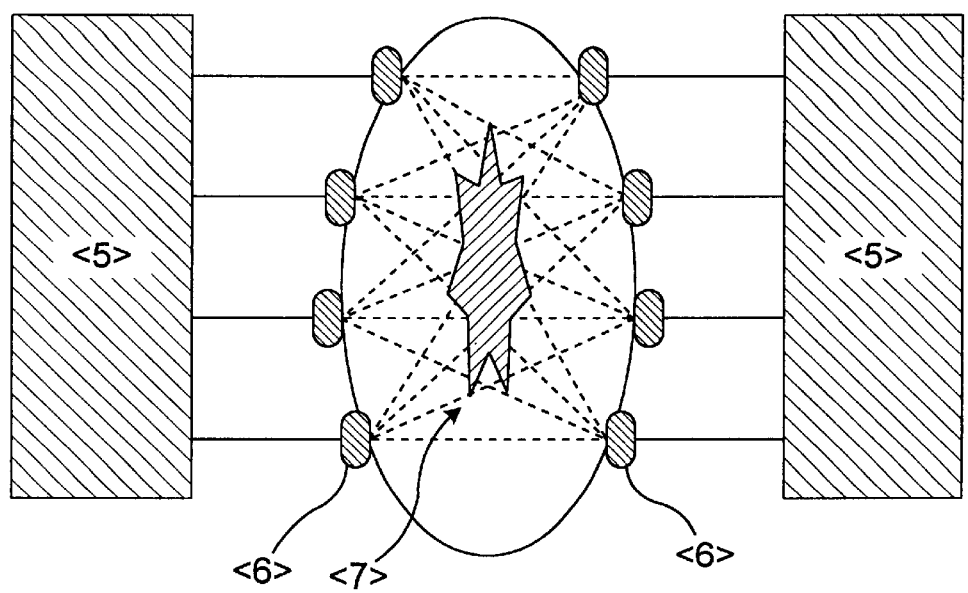
F I G. 6a
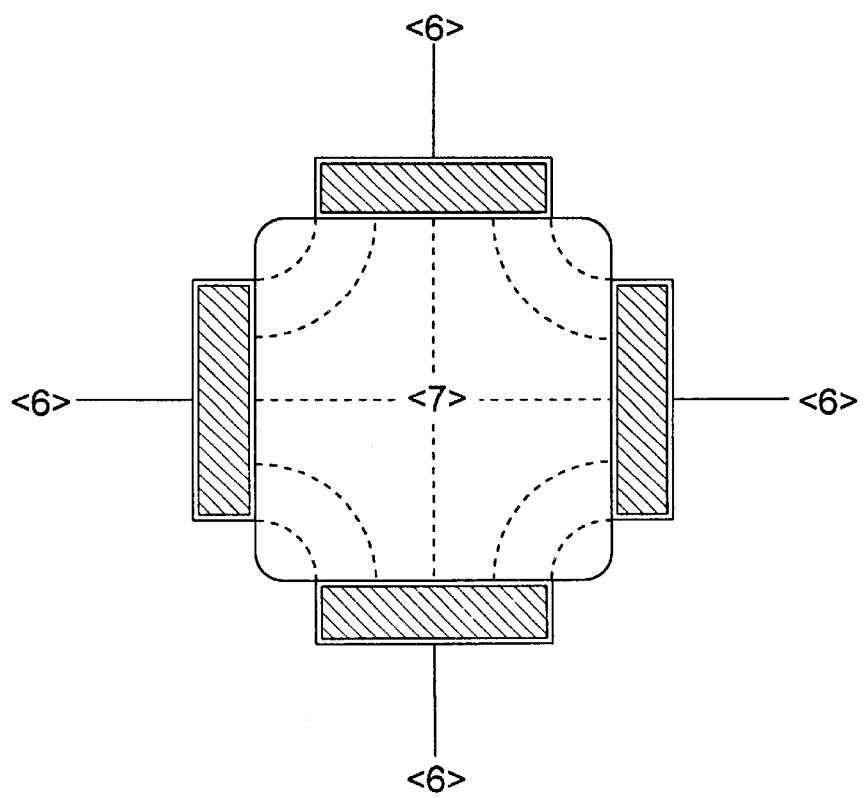
F I G. 6b

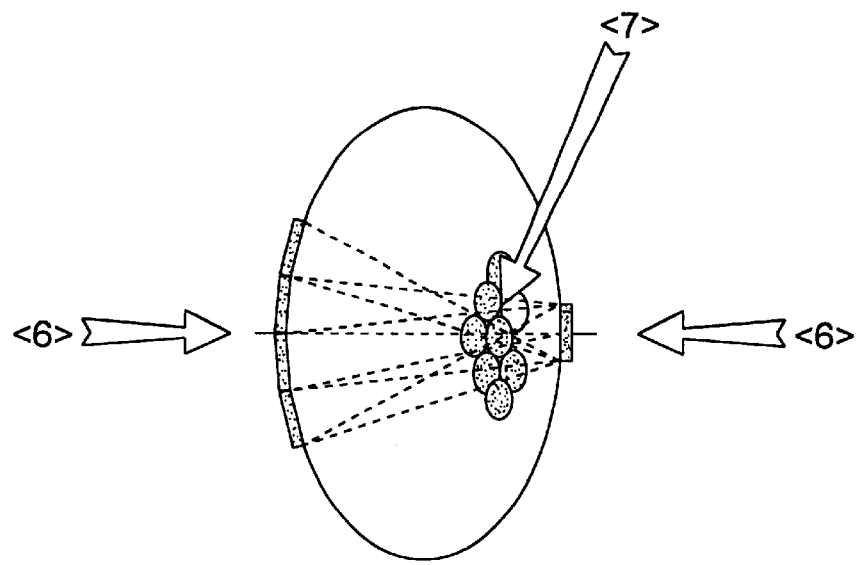
F I G. 6c
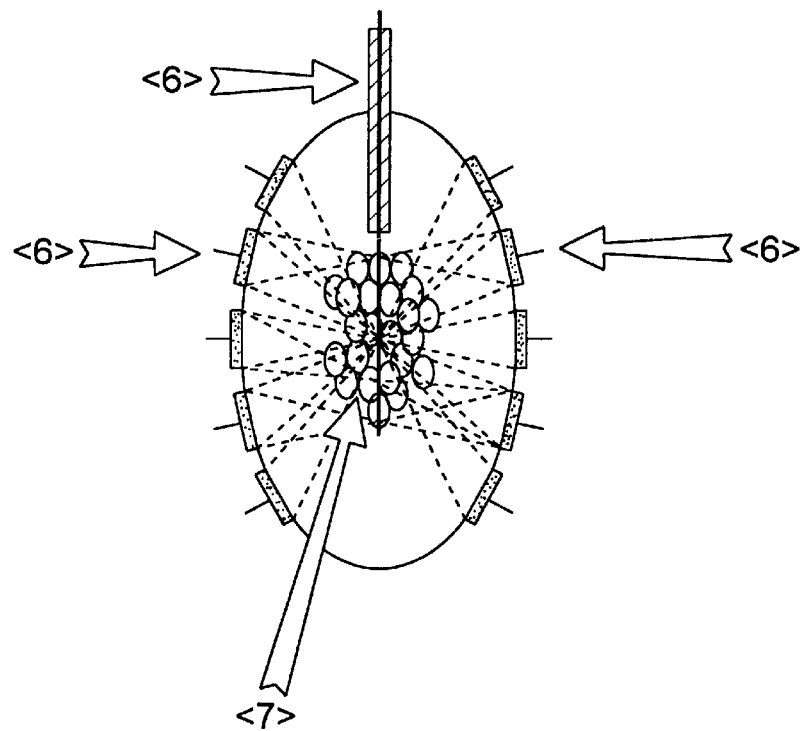
F I G. 6d

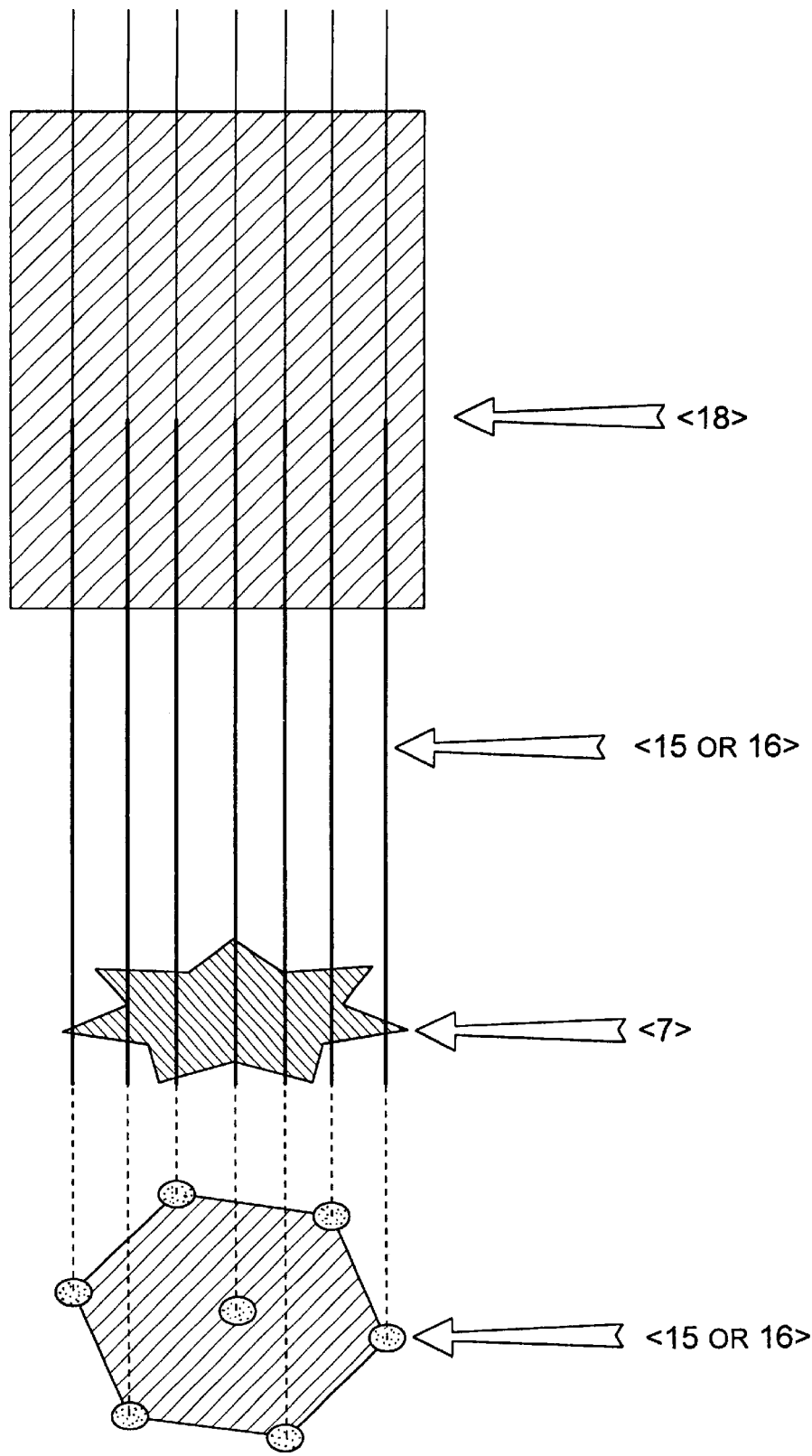
F I G. 8c

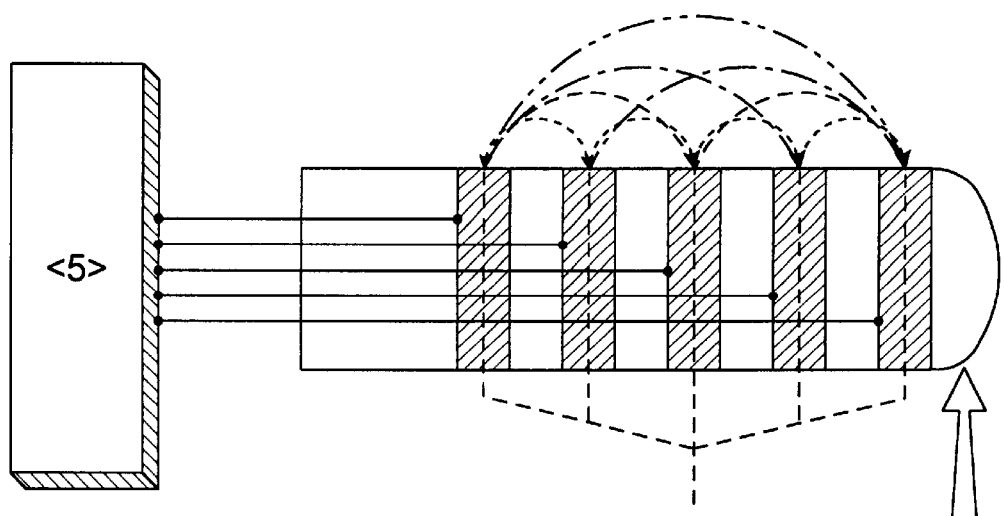
F I G. 9a
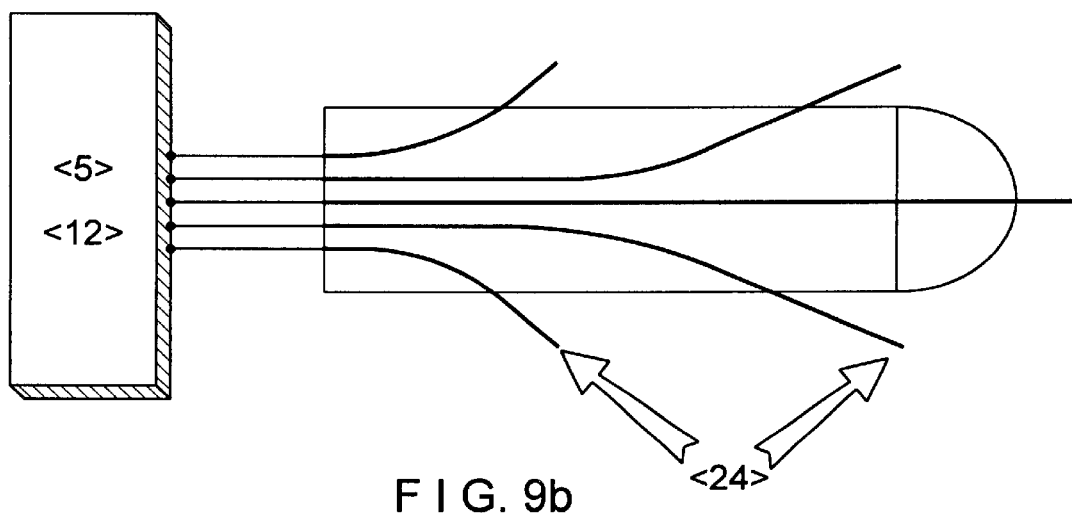
F I G. 9b
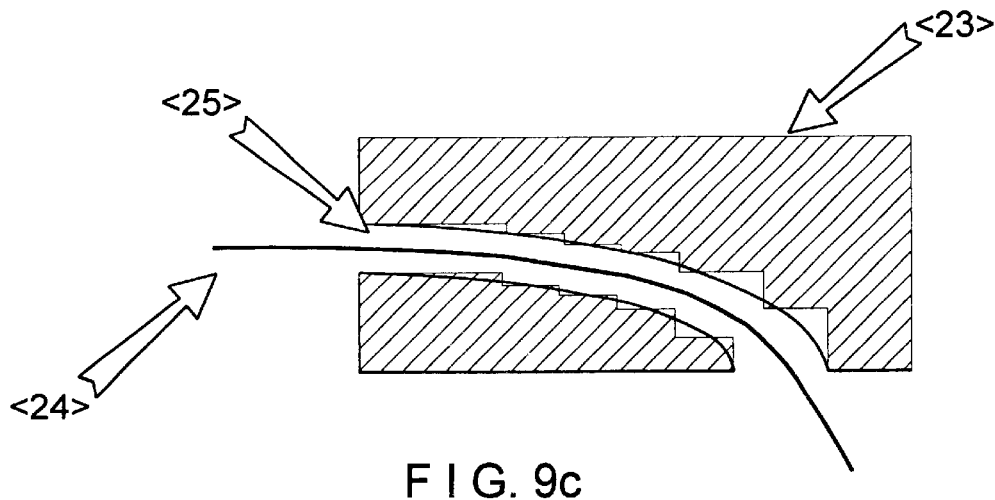
F I G. 9c

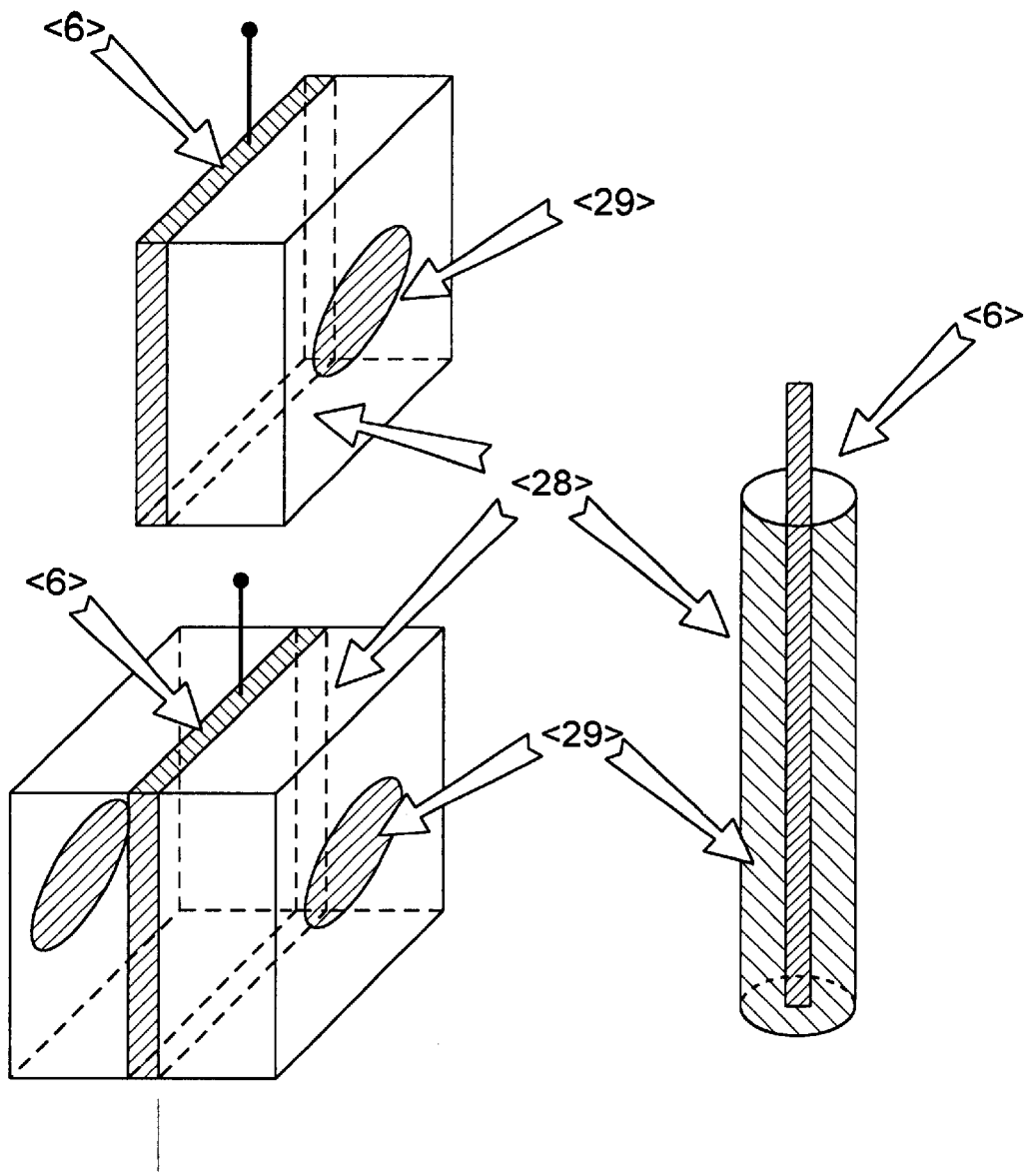
F I G. 10

METHOD AND AN APPARATUS FOR TREATING TUMORAL DISEASES (CANCER)

FIELD OF INVENTION

The present invention relates to a method and an apparatus for generating pulses of electric fields in a resricted area of a human or an animal, according to the preambles to the independent claims.

BACKGROUND OF INVENTION

The forms of therapy which are routinely applied in modern medicine for tumoral therapy often fail to achieve local tumor control, which is the cause of death of roughly 30% of cancer patients. It is, therefore, important to develop novel and improved techniques for local and regional tumor treatment.

In today's medical care, radiation therapy, also known as radiation treatment, surgery and combinations hereof are the most commonly employed methods for treating malignant tumors. Roughly every second patient suffering from infiltrating cancer is treated by radiation therapy, but only roughly half of these patients are cured. Such failure depends, on the one hand, on the presence of a wider spread disease (distant metastasis) or recurrence (a regrowth of a tumor in the treatment region), and, on the other hand, because certain tumor forms are resistant to radiation.

Attempts have been made, with varying success, to reinforce and improve the efficiency of radiation therapy in sterilizing tumors. For example, use has been made of more sophisticated radiation therapy techniques, such as stereotactic treatment, "conformal radiotherapy" of changed fractioning or added medication to increase the radiation sensitivity in the tumors.

Use is also made of heat as adjuvant to ionizing radiation which, for certain tumor forms, may increase the number of complete remissions by up to a factor of two.

It is obvious that there are both desires and needs in the art for a more efficient technique for treating tumors.

SUMMARY OF INVENTION

The characterizing clauses of the independent claims disclose a technique which entails a substantial improvement of the efficiency of the radiation therapy in sterilizing tumors.

The present invention relates to an apparatus which includes means for subjecting a tumor in a human or in an animal to one or more pulses of an electric field with a field strength adjustable for the pertinent treatment field, and means for ionizing radiation treatment of the tumor.

The present invention also relates to a method of treating tumors by a combination of ionizing irradiation and of pulses of electric fields which, in the tumor, have a field strength exceeding a predetermined level.

Expedient embodiments of the present invention are further disclosed in the appended subclaims.

In the application of the present invention, it has proved that the survival of tumor cells has been reduced substantially if they are first treated with ionizing radiation and thereafter exposed to pulses of electric fields with an electric field strength exceeding a certain level. This survival has fallen by a factor of 10 compared with survival in exclusively ionizing radiation. The tumors in rats have completely disappeared when they were treated with a combination of ionizing radiation and electric fields with a field strength exceeding a certain level.

BRIEF DESCRIPTION OF THE DRAWINGS

The present invention will be described in greater detail below with reference to a number of figures, in which:

FIG. 5 is a block diagram of one embodiment of a combination of means for the generation of electric fields in a resricted region in a human or an animal;

FIG. 6a–d show embodiments of electrode applicators for external treatment of tumors;

FIGS. 8a–d show embodiments of electrodes and electrode applicators designed for the interstitial treatment of tumors;

FIG. 9a–c show embodiments of electrodes and electrode applicators designed for the treatment of tumors in body cavities and in organs accessible via large vessels;

FIG. 10 shows embodiment of the electrodes in which these are designed for combination treatment with antitumoral medication.

DETAILED DESCRIPTION

Figure 1:
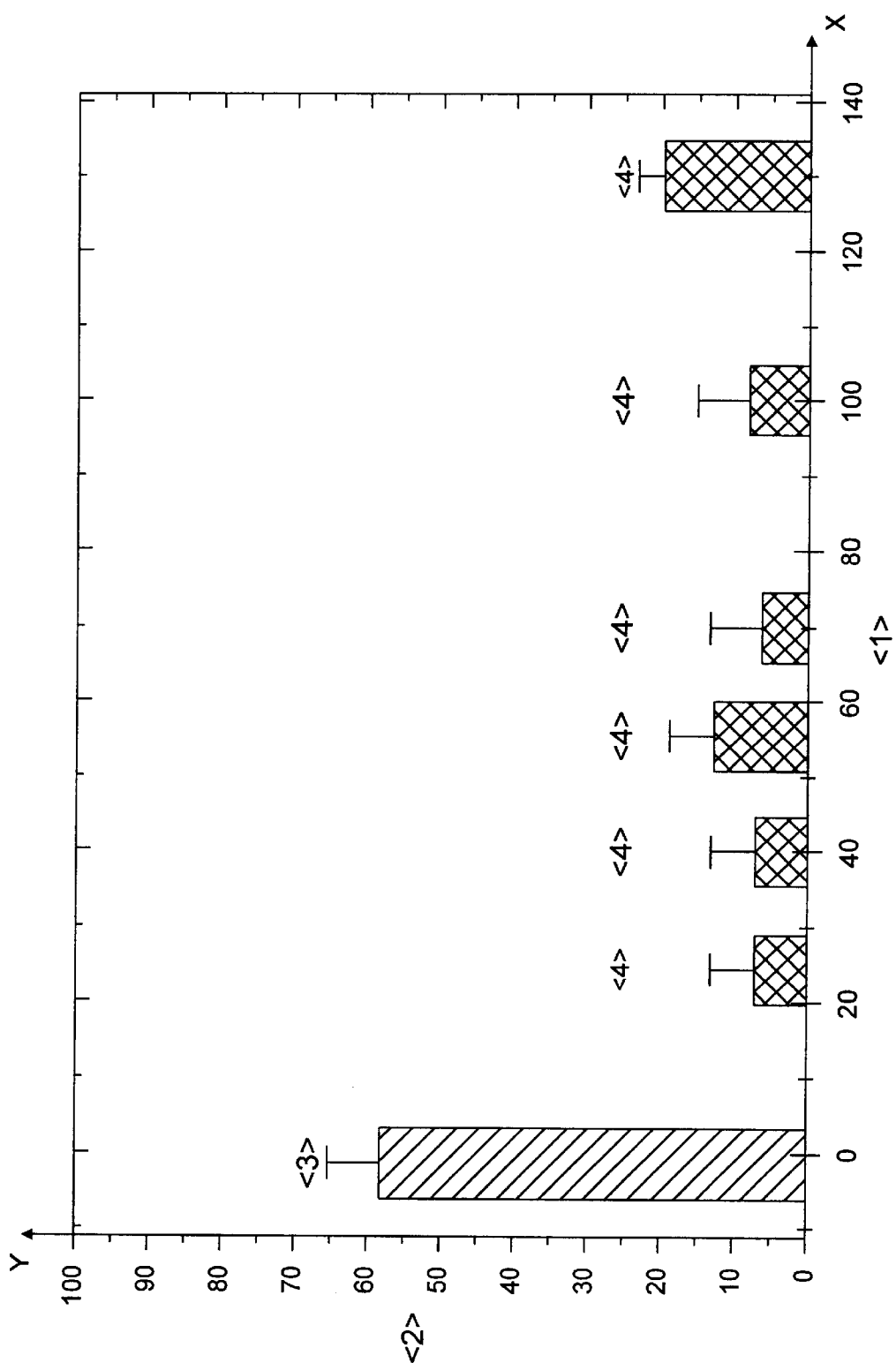
FIG. 1 shows the results of an experiment conducted on Jan. 11–15, 1996.

FIG. 1 shows, in a bar chart, the result of an experiment which was conducted on Jan. 11–15, 1996. Fibroblast cells (V79-cells) in 7 groups of small plastic tubes were placed in the experiment, in a water bath and were irradiated with ionizing radiation to a radiation absorbed dose of 2 Gy. $^{60}$Co gamma radiation was employed for the irradiation.

Within two hours, the V79-cells were exposed, in 6 of the groups, to a sequence of 8 brief (1 ms) pulses of electric fields of high electric field strength which passed through the cells. The electric fields were generated by electric high voltage pulses. The sequences of the electric fields applied to the cells in each one of the groups at different points in time after the $^{60}$Co gamma radiation. The high voltage pulses were of exponential form with a time constant of 1 ms and of an amplitude which generated an electric field with a maximum field strength corresponding to approx. 1600 V/cm through the cells. The pulses were repeated at 1 s intervals.

FIG. 1 show the outcome of the treatments of the V79-cells described in the two preceding paragraphs. The X-axis shows "time in minutes between the $^{60}$Co gamma radiation and the high voltage pulses", and the Y-axis shows the "percentage surviving cells". The first bar in the histogram shows the survival of cells after radiation treatment alone. With only this treatment, roughly 55% of the cells survived. The remaining bars in the bar chart show the survival when the $^{60}$Co gamma radiation was combined with the pulses of electric fields. When the pulses were applied within two hours from the $^{60}$Co gamma radiation, survival level fell to a mean count of less than approximately 10%.

The combination of radiation treatment of tumors and the generation of electric fields through them will, hereinafter, be designated as a rule "electrodynamic radiation therapy" or "electrodynamic radiation treatment". This expression is employed regardless of whether the radiation treatment precedes the treatment with electric fields, whether the radiation treatment takes place after the treatment with electric fields or whether the two treatments wholly or partly overlap one another.

Figure 2A:
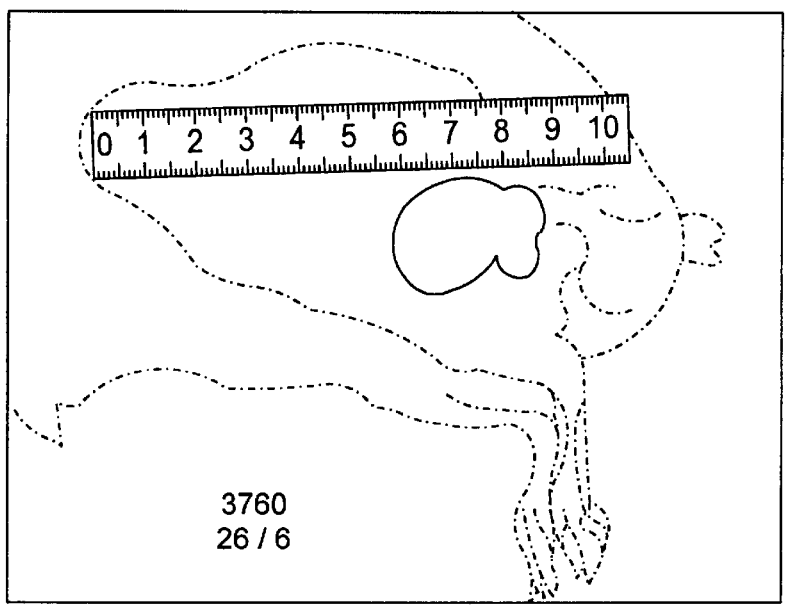
FIGS. 2a–c show photographs of a tumor in a rat.
Figure 2B:
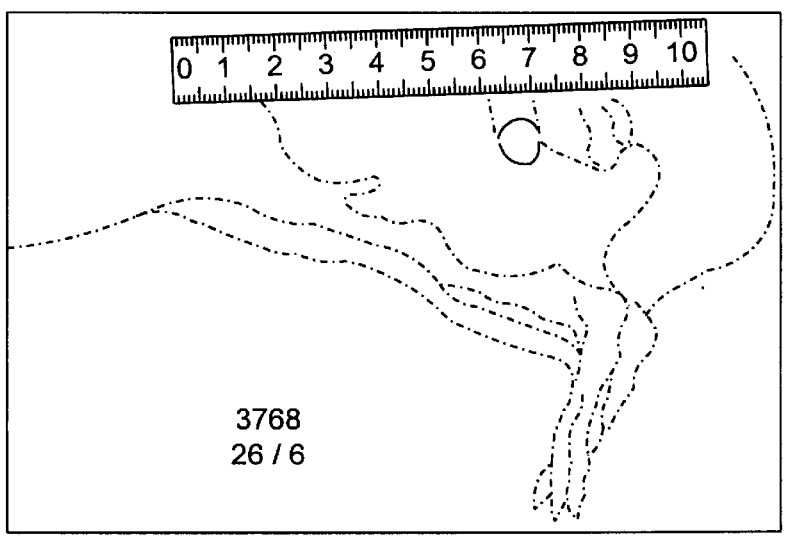
Figure 2C:
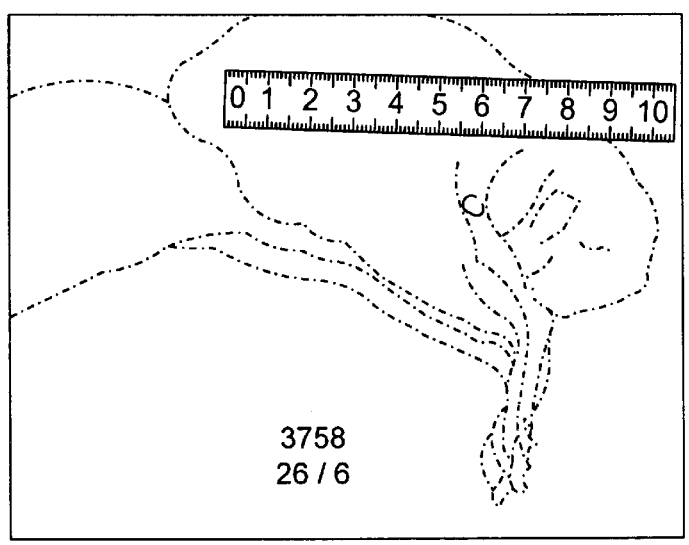
Figure 3:
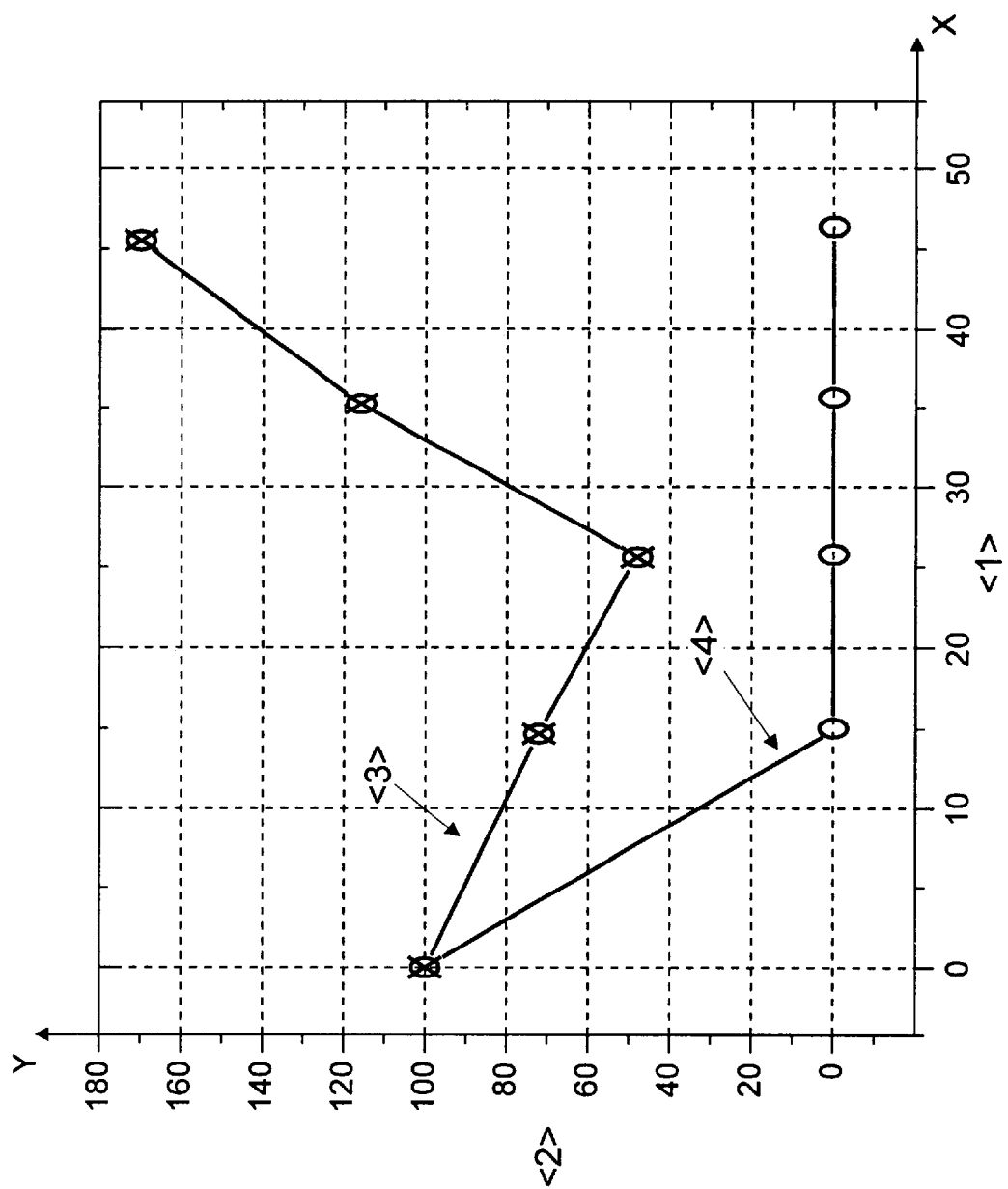
FIG. 3 shows the mean value of tumor size as a percentage of the initial size in tumors according to FIG. 2.

FIG. 2 and FIG. 3 show the results of an animal experiment with tumor cells implanted in the leg flank of rats. After approx. 3 weeks, palpable tumors developed. The tumors were treated daily for 4 days (May 21–24, 1996), partly with $^{60}$Co gamma radiation alone to an absorbed dose of 2 Gy, and partly with electrodynamic radiation treatment with (2 Gy+16 pulses of field strength approx 1300 V/cm in the tumor).

FIG. 2a shows a photograph of an untreated tumor in a rat, FIG. 2b shows a photograph of a tumor in a rat 47 days after radiation treatment of the tumor with 4×2 Gy $^{60}$Co gamma radiation, and FIG. 2c shows a photograph of a rat 47 days after electrodynamic radiation treatment of the tumor: 4×(2 Gy+16 electric pulses approx. 1300 V/cm, 1 ms, 1 s$^{-1}$). With electrodynamic radiation treatment, no palpable tumor remains. The treatments with the electric fields were conducted each time after the radiation treatment and within one (1) hour.

FIG. 3 shows the mean value of "tumor size as a percentage of initial size" (the Y-axis), partly after solely radiation treatment <3> with $^{60}$Co gamma radiation 4×2 Gy, and partly after electrodynamic radiation treatment <4>, with 4× (2 Gy+16 pulses at approx. 1300 V/cm in the tumor). The measurement points show the mean value of the tumor size for 4 conventionally radiation treated <3> and 3 electrodynamically radiation treated rats, respectively, <4> at different times in days after the treatment (the X-axis) Also in this experiment, treatment with electric fields took place after the radiation treatment.

The mean value of tumor size at different points in time after the treatment for 4 radiation <3> and 3 electrodynamically radiation treated <4> rats, respectively, with tumors shows that the tumors treated with electrodynamically radiation treatment disappeared rapidly and without any recurrence or regrowth, while only conventional radiation treatment gives a partial reduction of the tumor size, with continued tumor growth after approx. 3 weeks.

It is obvious that, in radiation treatment of tumoral diseases, the effect of the treatment is reinforced by combining the radiation treatment of the tumors with short intensive pulses of electric fields through the tumors. Experiments conducted indicate that, for certain types of tumors, the treatment with electric fields should be conducted before the radiation treatment, while for other types the treatment with electric fields and radiation treatment should wholly or partly overlap one another.

Examples of ionizing radiation suitable for combination with an electric field through the tumor are:

1. Gamma radiation and electron radiation from encapsulated radioactive preparations (e.g. $^{60}$Co, $^{137}$Cs, $^{226}$Ra, $^{192}$Ir, etc.),
2. Photon radiation from X-ray tubes and linear accelerators;
3. Electron radiation from accelerators (10 keV–50 MeV);
4. Proton radiation, heavy ions, neutrons;
5. Radiation from applied or injected radioactive isotopes, so-called radioactive medicines (alpha, beta, gamma radiation, auger electrons, conversion electrons and characteristic X-ray radiation; and
6. Neutron radiation from nuclear reactors used in neutron capture therapy (in, for example,boron reactions so-called BNCT It may be ascertained that, as a rule, an improvement will be obtained of the treatment result in irradiation of tumors with ionizing radiation in combination with the tumors also being exposed to electric fields of a field strength exceeding a certain level. This applies regardless of the employed type of ionizing radiation.

Figure 4:
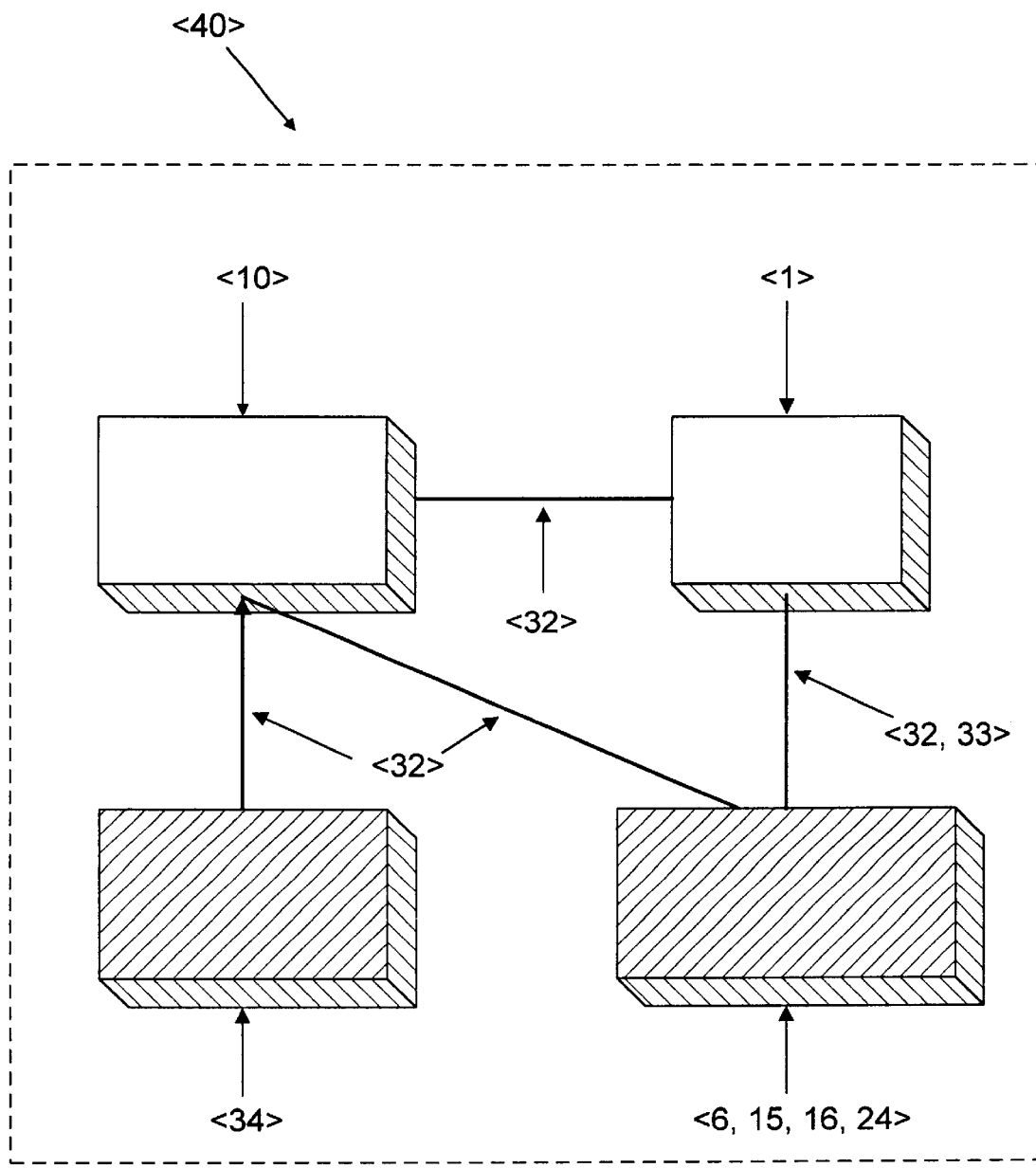
FIG. 4 is a block diagram showing a schematic apparatus for applying an electric field and/or ionizing radiation in a resricted region of a human or an animal.

FIG. 4 shows the present invention with the aid of a block diagram. The schematically illustrated apparatus 40 shown in the Figure comprises a high voltage generator 1, a radiation emitter 34 and electrodes 6,15,16,24 As a rule, a registration and conversion device 10 is also included in the apparatus, for example a computer or a microprocessor 10. Hereinafter, the word computer will generally be employed for the registration and conversion device, without any restrictive intent. Between the high voltage generator 1 and the electrodes 6,15,16,24, there is provided one or more signal communications 32 and electric leads 33. In those embodiments where the computer 10 is included, there are provided signal communications 32 between the computer and the electrodes 6,15,16,24 and the radiation emitter 35. While the signal communications 32 in the Figure are shown as directly connecting the computer and the electrodes, it will be obvious to a person skilled in the art that the apparatus as such also includes devices considered in the continuation of this description, such as switches 3, distributor units 4, electrode applicators 5, etc. for controlling the voltage application of the electrodes and/or activation and deactivation of ionizing radiation, etc.

FIG. 5 schematically shows one embodiment of a combination of means for generating electric fields in an apparatus according to the invention. In the Figure, blocks are shown for a high voltage generator 1, a capacitor battery 2, a switch 3, a distributor unit 4 for distribution of high voltage pulses generated on discharge of the capacitor battery 2 through the switch 3 to an electrode applicator 5 and electrodes 6 intended to be placed in or adjacent a tumor 7. The high voltage generator 1, the capacitor battery 2, the switch 3 and the distributor unit 4 are, by means of electric leads 33, connected in series to one another. Between the distributor unit 4 and the electrode applicator 5, there are provided at least one electric lead 32 and at least one signal communication 32. Via the signal communication 32, the distributor unit 4 controls the voltage application of the electrodes of the electrode applicator which, via the electric leads 33 are inter-connected with the distributor unit 4 and, via the electric lead 33, to the switch 3. In one alternative embodiment, each electrode 6 is electrically connected to the switch 3 by an electric lead 33.

As a rule, the switch 3 or the electrode applicator applies voltage simultaneously only to two electrodes 6, while other electrodes are permitted to assume that potential which is determined by the placing of the electrode in the treatment region. The term voltage application also encompasses, in this context, the feature that one or more electrodes are earthed (have zero potential). The switch 3 and/or the electrode applicator 5 are disposed, if desired, to permit pairwise voltage application of all electrodes which are applied in the treatment region. It will be obvious to a person skilled in the art, that, in certain embodiment, these means provided, on voltage application, to allocate to several electrodes a substantially corresponding potential.

Via signal communications, all units are connected to a registration and conversion device 10, also designated computer 10. The computer 10 constitutes a control and monitoring device for the function of the apparatus.

The expression electrode applicator 5 signifies a retainer for the electrodes 6, the retainer being designed so as to facilitate the correct application of the electrodes to or in the treatment region.

The computer is set generally for the high voltage pulses to include the following data:

| repetition frequency | approx. 0.1–10 pulses/second |
| --- | --- |
| amplitude | approx. 500–6000 V |
| pulse length | approx. 0.1–2 ms |
| number of pulses | 5–20 per treatment. |

The pulses are applied before, during or just after the radiation treatment. Examples of employed pulse forms are square pulses with a pulse length of 0.1–2 ms or exponentially fading pulses with a time constant RC approximately equal to 0.1–2 ms.

In embodiments in which the high voltage generator 1 emits modulated A.C. voltage at high frequency, approx. 40–100 kHz use is made of a modulator instead of capacitor battery and switch so as to form brief, modulated high frequency pulses of a pulse length within the range of between approx. 0.1 and 10 ms.

As will be apparent from the embodiment illustrated in FIG. 5, the apparatus generally also includes sensors 8 intended to be applied to the patient in the treatment region. The sensors are connected via a detector interface 9 to the registration and conversion device 10. On application of the treatment pulse, a signal is generated in the sensors 8 which, via the interface 9, is transferred to and registered in the computer 10. From the signals measured, the computer calculates the electric field strength induced by the pulse and the electromotoric force in different parts of the treatment region 7. These signals entail that the computer 10 emits signals to the high voltage generator/capacitor battery (feedback connection) to adjust the amplitude of the generated pulses such that the predetermined field strength is attained in the treatment region. This monitoring and adjustment takes place continuously during the application of the pulses.

FIGS. 6a–d show embodiments of electrode applicators 5 for the external treatment of a tumor, with the electrodes 6 applied in a resricted region to the patient and in different configurations around the tumor 7. FIGS. 6a and 6b show how, by cruciform application of the electric high voltage pulses to different combinations of two electrodes 6, it will be achieved that, as marked in the Figure by the electric field force lines, the electric field passes through all parts of the tumor 7.

FIGS. 6c–d show how electrodes are designed with abutment surfaces of different sizes in order that the field lines be focused to the desired treatment region. Electric high voltage pulses whose voltage is adjusted in response to the distance between the electrodes are applied during, immediately before or after the radiation treatment. The voltage is adjusted in accordance with the relationship:

Voltage=(constant)×(the distance between the pairwise electrodes).

The value of the constant is varied in dependence upon the type of tumor and is selected as a rule to values of between approx. 500 and 3000 V/cm.

Figure 7:
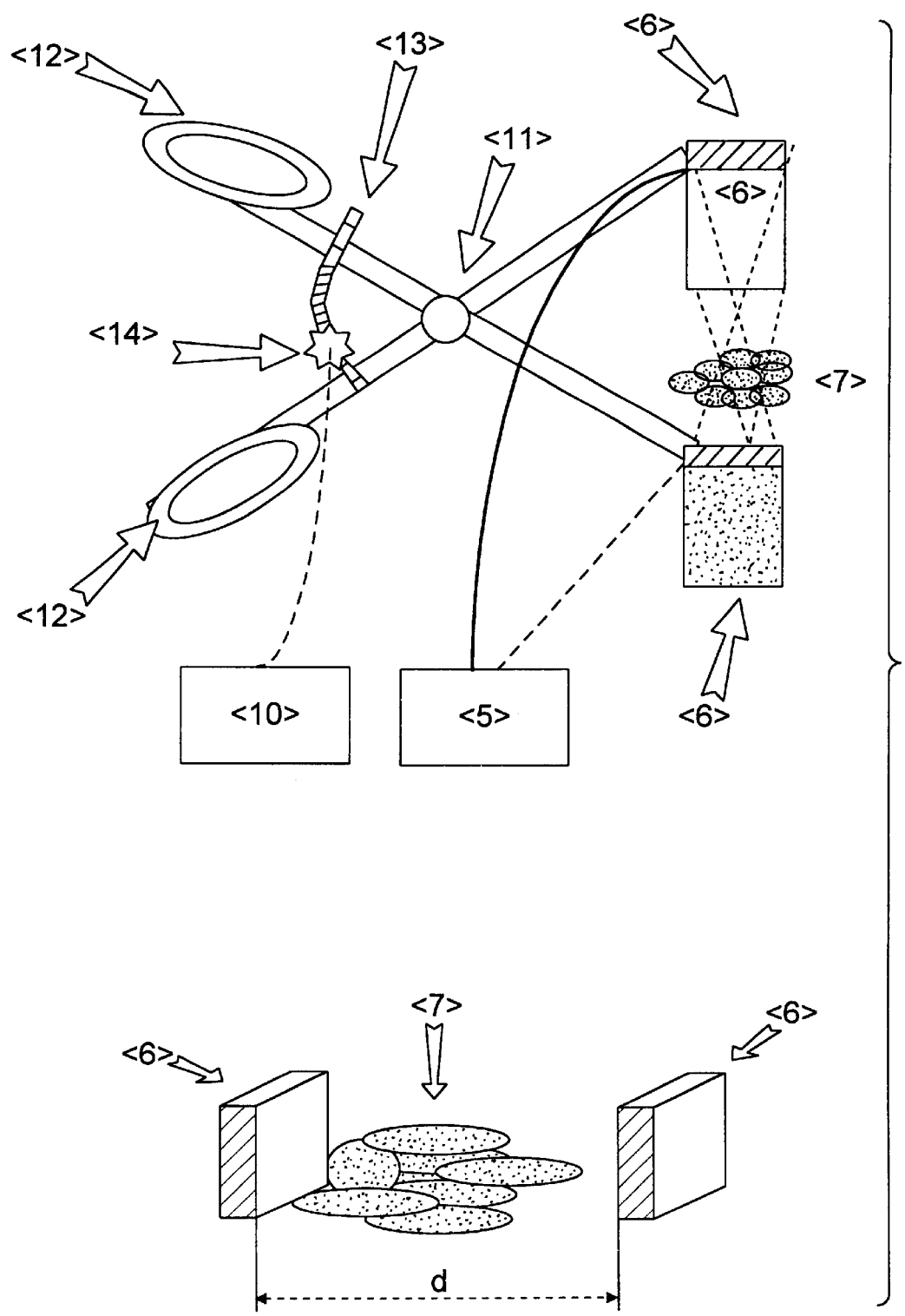
FIG. 7 shows one embodiment of an electrode applicator for intra operative treatment of tumors and for the treatment of superficial tumor nodules.

FIG. 7 shows one embodiment of an electrode applicator 5 for intra-operative treatment and treatment of superficial tumor nodules 7. The electrode applicator has scissor-shaped formation and comprises two shanks 12 of electrically insulating material (e.g. Teflon™) which are movably interconnected to one another in a journal 11. The shanks are provided with a gripping block 13. At one end of each shank 12, the shanks are provided with finger grips and, at the other ends, with electrodes 6 which grasp about the tumor nodules 7. The gripping block 13 fixes the shanks 12 in the set position. The voltage of the electric high voltage pulses is adjusted in response to the size of the tumor 7 with the aid of a distance sensor 14 integrated in the electrode applicator and connected to the computer 10. The voltage is determined in accordance with the relationship:

Voltage=(constant)×(the distance between the pairwise electrodes).

The value of the constant is adapted in response to the type of tumor and is generally selected within the range of between approx. 500 and 3000 V/cm.

Figure 8A:
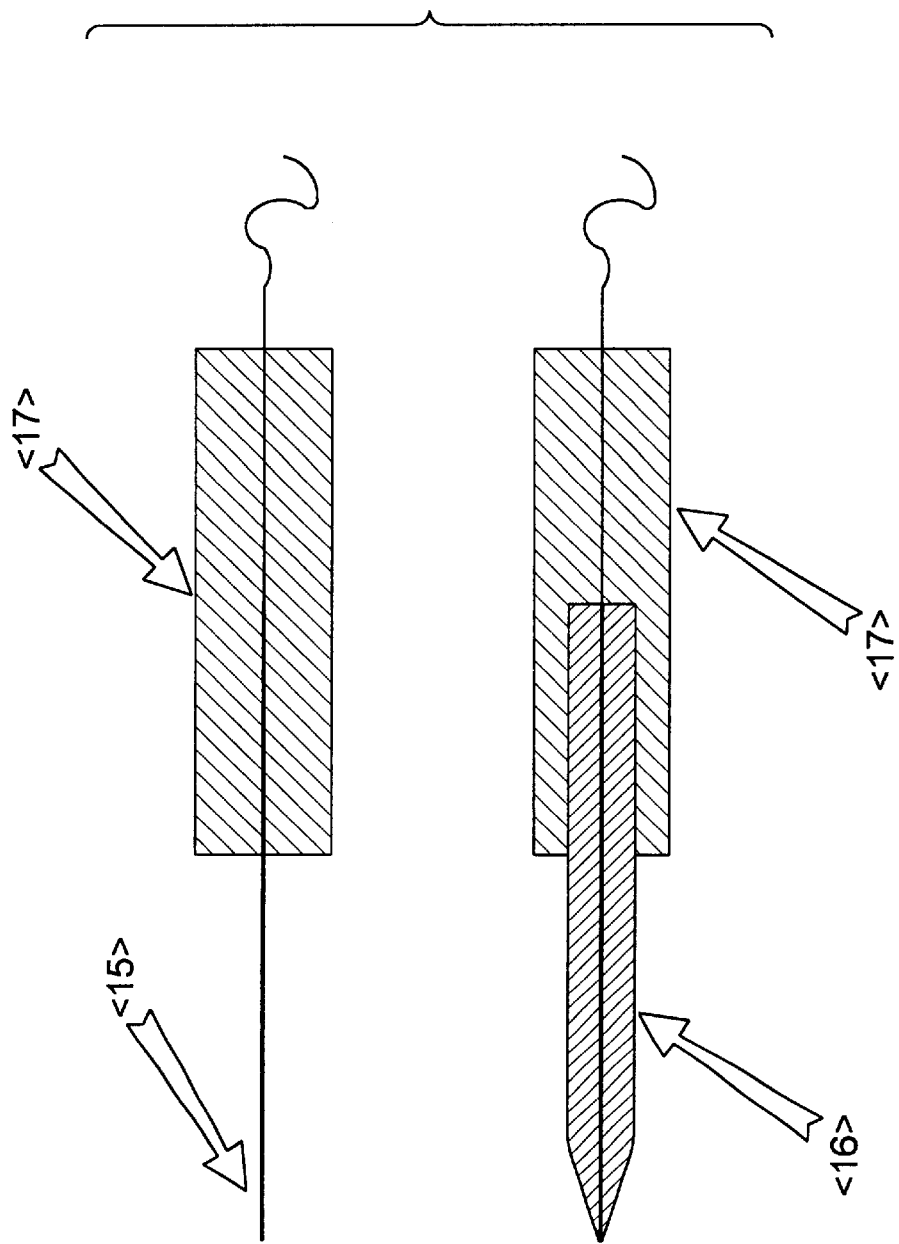
Figure 8B:
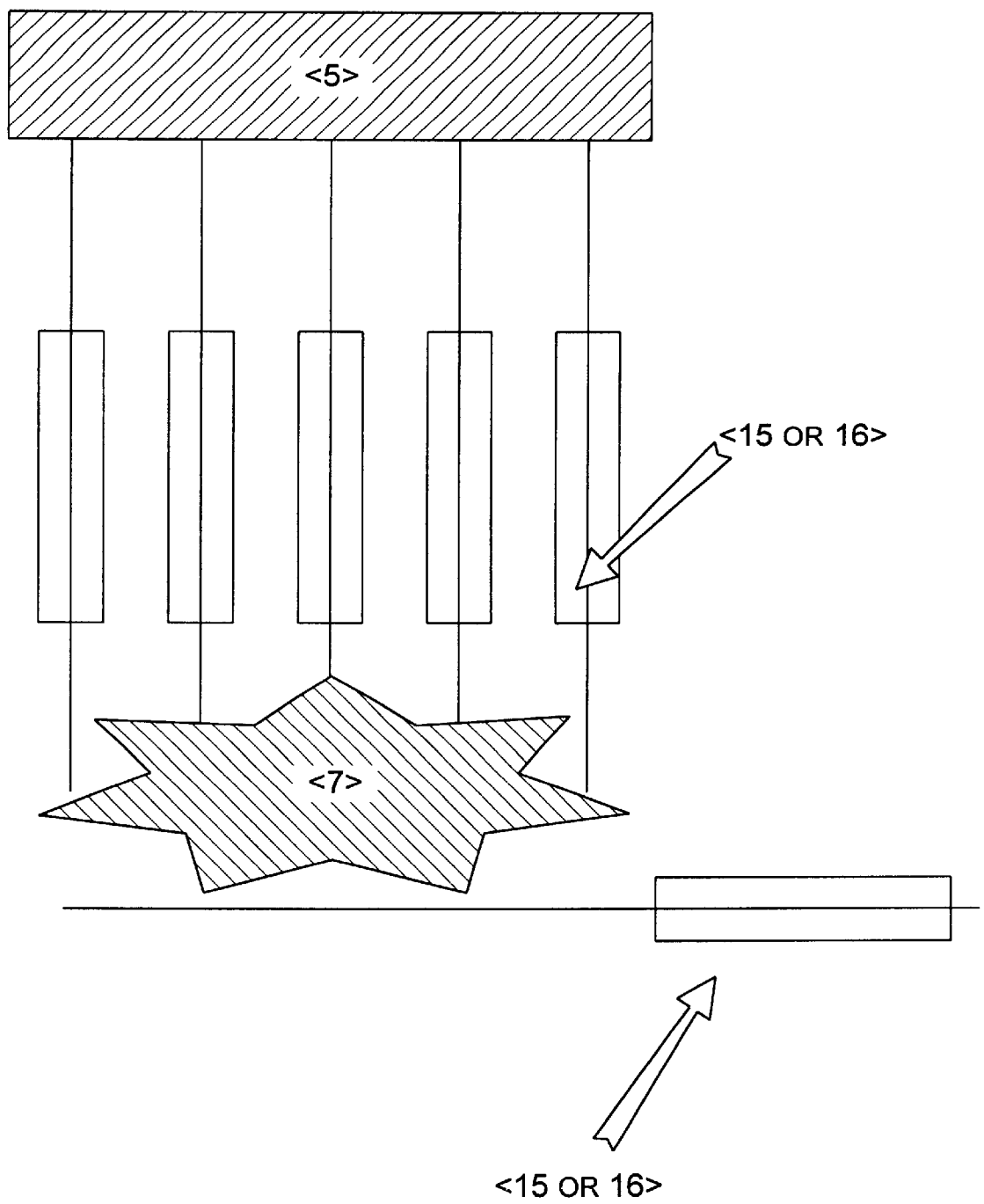
Figure 8D:
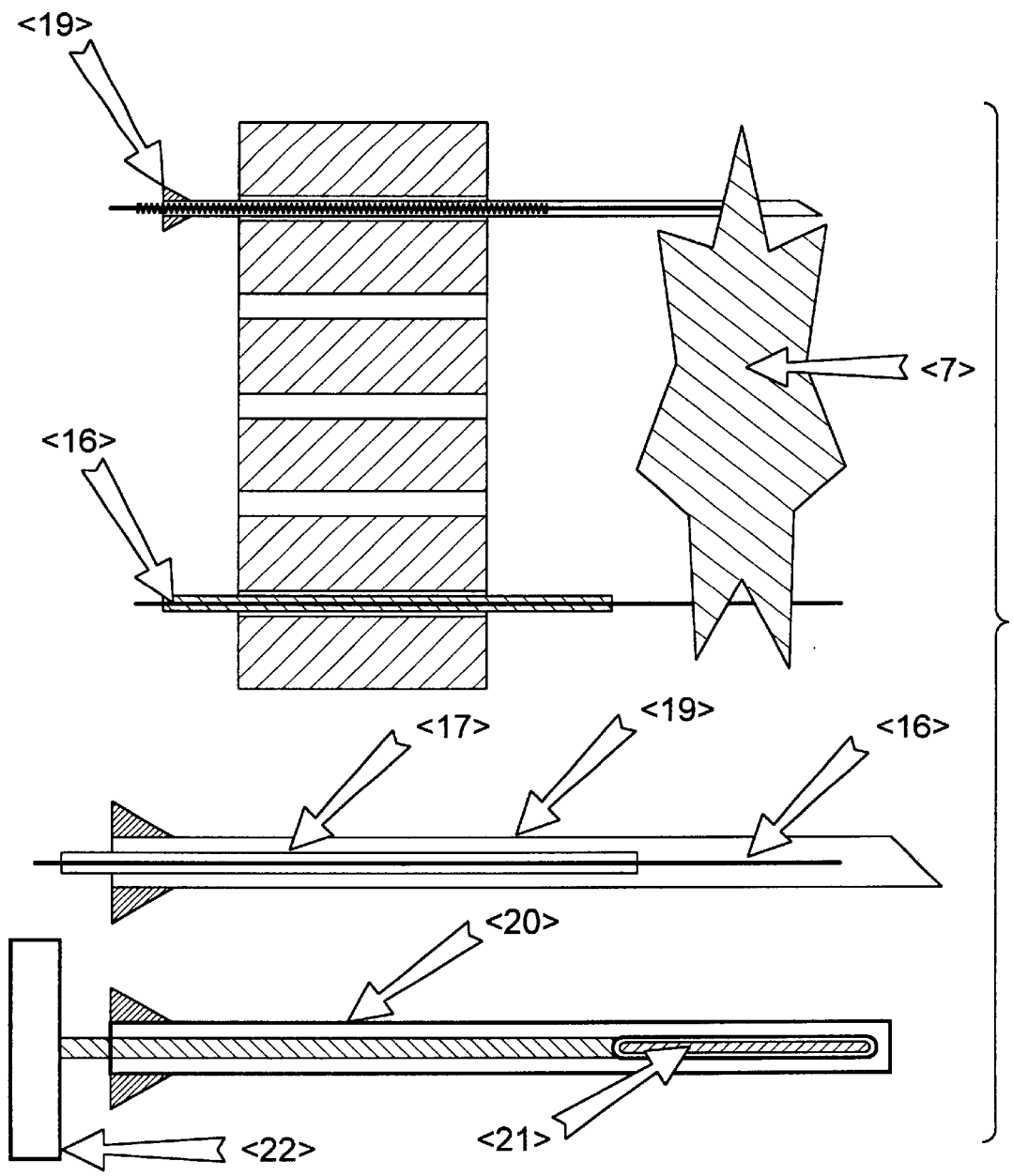

FIGS. 8a–d show embodiments of electrodes 15,16 and a fixture 18 for the electrodes, in which the electrodes and the fixture are suitable to be employed for interstitial treatment of both superficial and profound tumors. In FIG. 8a, the electrode 15,16 are shown in two different embodiments, namely in one embodiment in which the electrodes 15 are needle-shaped, and one embodiment in which the electrodes 16 are stiletto-shaped, and one embodiment in which the electrodes 16 are stiletto-shaped. Each one of the electrodes 15,16 is provided, in a region 31 most proximal their one end, with an electric conductor 32 for connection to the high voltage generator 1. The above-mentioned portion is provided with an electrically insulating layer 17 or an electrically insulating sleeve 17 in which the electrode is inserted.

The electrodes are applied in different configurations in and about the tumor 7, either directly by free hand, or with the aid of a perforated electrode applicator (fixture) 18. The electrode applicator is generally designed to be removed from the electrodes 15,16 once these have been applied to the patient. It will thereby become possible to allow the electrode to remain in position in the patient in order to be employed on several subsequent treatment occasions. Alternatively, the electrode applicator is removed together with the electrodes 15,16 after each treatment. Also in interstitial treatment, electrodes with surfaces of different sizes occur for controlling the extent of the electric field.

The parts of the electrodes 15,16 which are intended to be placed in the patient in order to cover the extent of the tumor 7 are, for example, manufactured from stainless steel of a quality which tallies with or corresponds to that employed for injection syringes, or are manufactured from other tissue-friendly metal such as noble metal.

The remaining portion of the electrodes forms a insulated portion 17 with leads 33 for the high voltage pulses. In the employment of soft, flexible leads, the electrodes is placed in a large calibre cannula 19 which, after application of the electrodes in the patient, is withdrawn, the electrodes remaining in position in the tissue.

In certain embodiments, the electrodes consist of radioactive metal (e.g. iridium 192, cobalt 60) or are surface-coated with radioactive substances (e.g. iodine 125). In other embodiments, they are designed as tubes 20 of inert metal which are charged with radioactive material (e.g. $^{192}$Ir, $^{137}$Cs, $^{226}$Ra) which ideally takes place using a so-called after charge apparatus 22. Electric voltage pulses are supplied to the electrodes in the treatment region before, during or immediately after the radiation treatment. The pulses have a voltage which is determined by the distance between the electrodes. The voltage is set in accordance with the relationship:

Voltage=(constant)×(the distance between pairwise electrodes).

The value of the constant is selected in dependence upon the type of tumor, as a rule within the range of between approx. 500 and 3000 V/cm.

FIGS. 9a–c show electrodes 24 for the treatment of tumors in living organs accessible via, for example, large vessels, or bodily cavities, for example respiratory tracts, urinary tracts or the intestinal tract. The electrodes are disposed on the surface of a cylinder-like electrode applicator 23 of insulating material. In certain embodiments, the electrodes are designed such that they are passed into the tissue through channels 25 in the applicator 23, operated by a remote control. As is apparent from FIG. 9c, the embodiment of the channel 25 disclosed in the previous sentence discharges in the circumferential surface of the electrode applicator, whereby the electrodes 24, on their displacement, are guided into tissue which surrounds the electrode applicator. In certain embodiments, the applicator is disposed to be supplied with radioactive preparations, whereby the applicator also forms a radiation device. The applicator is disposed to be supplied with the radioactive preparation manually, or by means of an after charge device 22. Electric high voltage pulses whose voltage is adjusted in response to the distance between the electrodes are applied before, during or immediately after the radiation treatment, in accordance with the relationship:

Voltage=(constant)×(the distance between pairwise electrodes).

The value of the constant depends upon the type of tumor. As a rule, the value of the constant is selected within the range of approx. 500 to 3000 V/cm.

The field lines in FIG. 9a indicate the extent of the electric field lines in the tissues.

For intracavital treatment of tumors in different, irregularly shaped bodily cavities (e.g. the oral cavity, respiratory tract, oesophagus, stomach, uterus, bladder, urether, rectum) electrode applicators 23 are, as is apparent from FIGS. 9a–c, applied specifically designed in accordance with the configuration of the cavity with electrodes applied on the surface 24, or alternatively designed as needles which are passed into the tissue through ducts 25 by remote control. These applicators are suitable to be used, for example, for the treatment of lung cancer, liver tumors, renal tumors and tumors in the intestinal tract with reduced absorbed dose in order to reduce the side effects of radiation treatment in normal tissues. Prostate cancer is treated with applicators applied via the rectum and urether. These applicators are, in certain embodiments, designed to be charged with radioactive sources or radioactive material 21, either manually or by an after charge device 22.

Electric high voltage pulses whose voltage is adjusted in response to the distance between the electrodes are applied before, during or immediately after the radiation treatment. The voltage is adjusted in accordance with the relationship:

Voltage=(constant)×(the distance between pairwise electrodes).

The value of the constant is varied in dependence upon the type of tumor and is generally selected between approx. 500 and 3000 V/cm.

FIG. 10 shows an apparatus for the combination treatment with antitumoral medication, in which the electrode 6 is coated with a layer 28 of porous metal, glass, ceramics, inert plastic or other polymer which contains antitumoral medication 29 (e.g. bleomycin, platinol, taxol, monoclonal antibodies), genetic material (chromosomes, DNA), or radioactive substances (e.g. iodine 125, auger electron emitters). This type of electrode is well suited to be used in electrodynamic radiation therapy, since the high electric field strength increases the permeability of the tumor cells for the above-mentioned substances and thereby increases the antitumoral effect.

Figure 11A:
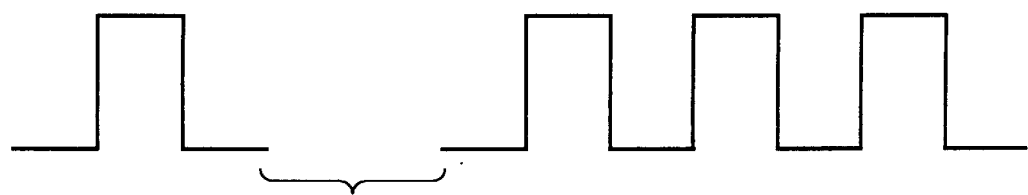
FIGS. 11a–e show examples of forms of voltage pulses applied to the electrodes.
Figure 11B:
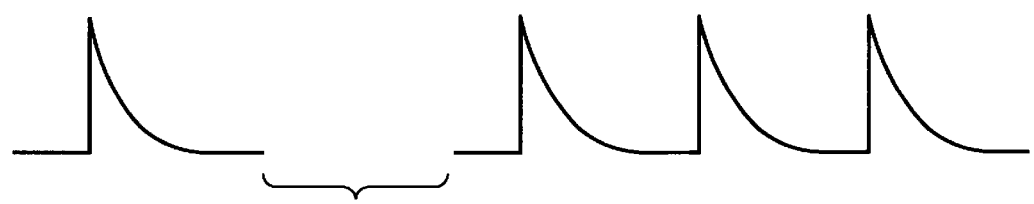
Figure 11C:
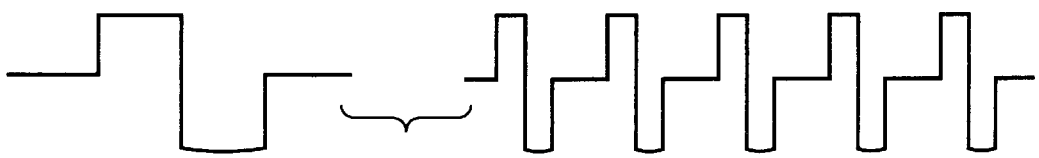
Figure 11D:
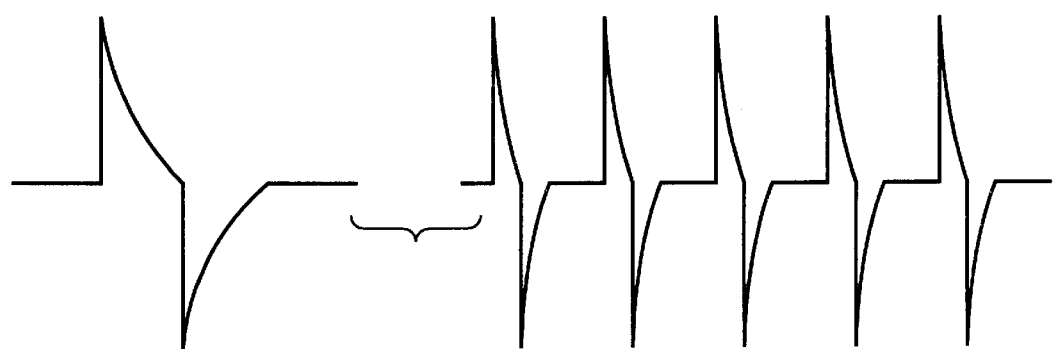
Figure 11E:
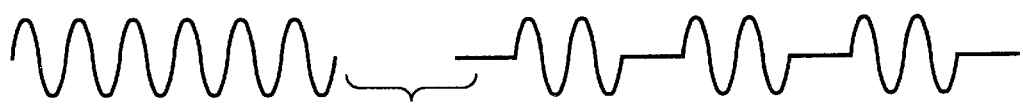

FIGS. 11a–e show examples of pulse forms in the voltage pulses which are pairwise applied to the electrodes 6,15,16, 24. In the Figures, the height of the pulses represents the voltage between two electrodes. The width of the pulses represents the length of the pulse. FIGS. 11a and 11c show examples of square pulses, FIG. 11b and 11d show examples of pulses whose voltage fades with time, and FIG. 11e shows pulses of A.C. voltage. FIGS. 11c and 11d show voltage pulses in which, analogous with that which applies to A.C. voltage, the electrodes alternatively have the highest voltage, whereby a corresponding change takes place of the electric field between the electrodes.

In one realization of the present invention, the radiation emitter and the electrodes in certain embodiments together with the electrode applicator form a combined mechanical unit. This is of a design which make it possible, in a restricted region of a human or an animal, to apply both the radiation emitter and the electrodes in positions where the ionized radiation is directed towards the tumor and in which the electrodes have positions in which electric fields between them pass through the tumor. In other embodiments, these means constitute separate mechanical parts which, together, and where applicable, over time, form a system of means and devices of a composition corresponding to that disclosed above for the apparatus 40.

The present invention should not be considered as restricted to that described above and shown on the Drawings, many modifications being conceivable without departing from the scope of the appended Claims.

What is claimed is:

1. An apparatus (40) comprising a high voltage generator (1) for generating brief voltage pulses for voltage application of electrodes (6,15,16,24) included in the apparatus, or electrodes (6,15,16,24) connected to the apparatus, the apparatus including means (4,5) for distributing the voltage pulses to the electrodes (6,15,16,24) characterized in that the apparatus also includes means (34) for supplying ionized radiation to a tumor (7) existing in a human or in an animal, that the electrodes (6,15,16,24) are designed to be secured to a resricted region of the human or the animal, or designed to be inserted in said region in order, on treatment of the tumor, to form therebetween electric fields, that the fields have a field strength which exceeds a predetermined level, and that the electrodes are disposed, in the treatment, to be placed in or at the tumor (7) in positions entailing that the electric field passes through the tumor.

2. The apparatus as claimed in claim 1, characterized in that the apparatus includes sensors (8) for detecting electric fields formed by the electrodes (6,15,16,24), and that the sensors are connected to a registration and conversion device (10) for calculating the size of the electric field strength in the treatment region and, for regulating the amplitude of the voltage pulses applied to the electrodes, the registration and conversion device (10) is connected to the high voltage generator (1) and/or to means (2,3,4) connected in between the high voltage generator (1) and the electrodes (6,15,16,24).

3. The apparatus as claimed in claim 1, characterized in that the electrodes (6) are disposed to be excited alternatingly and only two at a time.

4. The apparatus as claimed in claim 1, characterized in that the apparatus includes sensors (14) for detecting the distance between the electrodes (6) in each pair of excited electrodes, and that the registration and conversion device (10) includes means for adjusting the voltage between the electrodes (6) in each pair of excited electrodes based on the distance between the electrodes.

5. The apparatus as claimed in claim 1, characterized in that the electrodes (6) are designed as needles (15) or stilettos (16).

6. The apparatus as claimed in claim 1, characterized in that the electrodes (6,15,16,24) are wholly surrounded by an electronically insulating layer (17) or have an electrically insulating layer which at least leaves an electrically conductive tip of the electrodes uninsulated.

7. The apparatus as claimed in claim 1, characterized in that an electrode applicator (5,23) is disposed for at least temporarily fixing the electrodes prior to placing of the electrodes on or in the treatment region.

8. The apparatus as claimed in claim 7, characterized in that the electrode applicator (23) is of a size and configuration which are adapted to the vessel, body aperture or bodily cavity where it is to be placed.

9. The apparatus as claimed in claim 7, characterized in that the electrode applicator (5) includes a fixture (18) for fixing the electrodes (15,16) in a fixed pattern.

10. The apparatus as claimed in claim 7, characterized in that the fixture (18) is provided with a number of holes for placing the electrodes in a desired pattern on each treatment occasion.

11. The apparatus as claimed in claim 1, characterized in that the apparatus includes at least one cannula (19) each one provided for temporarily enclosing an electrode.

12. The apparatus as claimed in claim 1, characterized in that the electrodes (6,15,16,24) consist of radioactive material or are designed with cavities for accommodating radioactive preparations (21).

13. The apparatus as claimed in claim 1, characterized in that the electrodes (6,15,16,24) are coated with a layer (27) of porous material for absorbing therapeutic substances (28).

14. The apparatus as claimed in claim 8, characterized in that the electrode applicator (23) is provided with electrodes (24) placed on the surface of the applicator, or that the electrodes (24) are placed in ducts (25) discharging in apertures in the surface of the applicator and displaceable by remote control in the ducts, and at least partly out through the apertures in order to be passed into the tissue surrounding the applicator.

15. A method of exposing a resricted region of a human or an animal to a treatment comprising generation of electric fields through tissue within the restricted region, characterized in that the treatment with electric fields is combined with a treatment by means of ionizing radiation, and that the treatment with the ionizing radiation takes place within a limited interval in time prior to or after the treatment with electric fields or in a time interval within which the treatment with electric fields and ionizing radiation wholly or partly overlap one another.

16. The method as claimed in claim 15, characterized in that the treatment is employed for sterilizing tumors.

* * * * *

UNITED STATES PATENT AND TRADEMARK OFFICE
CERTIFICATE OF CORRECTION

PATENT NO.   : 6,248,056 B1
DATED        : June 19, 2001
INVENTOR(S)  : Persson

It is certified that error appears in the above-identified patent and that said Letters Patent is hereby corrected as shown below:

<u>Title page,</u>
Insert -- [73] Assignee: Radinvent AB, Lund (SE) --.

Signed and Sealed this

Second Day of October, 2001

Attest:

*Nicholas P. Godici*

NICHOLAS P. GODICI
*Acting Director of the United States Patent and Trademark Office*

*Attesting Officer*